US00PP26617P2

(12) United States Plant Patent
Krejci

(10) Patent No.: US PP26,617 P2
(45) Date of Patent: Apr. 19, 2016

(54) ***LONICERA* PLANT NAMED 'DOLCE VITA'**

(50) Latin Name: ***Lonicera caerulea* var. *Kamtschatica***
Varietal Denomination: Dolce Vita

(71) Applicant: Frantisek Krejci, Ceska Trebova (CZ)

(72) Inventor: Frantisek Krejci, Ceska Trebova (CZ)

( * ) Notice: Subject to any disclaimer, the term of this patent is extended or adjusted under 35 U.S.C. 154(b) by 5 days.

(21) Appl. No.: 14/121,374

(22) Filed: Aug. 26, 2014

(51) Int. Cl.
*A01H 5/00* (2006.01)

(52) U.S. Cl.
USPC ..... Plt./226

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Lonicera* plant named 'Dolce Vita', characterized by its upright and outwardly spreading plant habit; vigorous growth habit and rapid growth rate; early and freely fruiting habit; large flavorful dark blue-colored fruits; and good garden performance.

3 Drawing Sheets

Botanical designation: *Lonicera caerulea* var. *Kamtschatica.*

Cultivar denomination: 'DOLCE VITA'.

BACKGROUND OF THE INVENTION

The present invention relates to a new and distinct cultivar of *Lonicera* plant, botanically known as *Lonicera caerulea* var. *Kamtschatica*, commonly referred to as Honeysuckle and hereinafter referred to by the name 'Dolce Vita'.

The new *Lonicera* is a product of a planned breeding program conducted by the Inventor in Vlčkov, Czech Republic. The objective of the breeding program was to develop new early fruiting *Lonicera* plants with large and flavorful fruits.

The new *Lonicera* plant originated from a cross-pollination conducted by the Inventor in May, 1998 of two unnamed seedling selections of *Lonicera caerulea* var. *Kamtschatica*, not patented. The new *Lonicera* plant was discovered and selected by the Inventor in June, 2001 as a single flowering plant within the progeny of the stated cross-pollination in a controlled environment in Vlčkov, Czech Republic.

Asexual reproduction of the new *Lonicera* plant by softwood cuttings in a controlled greenhouse environment in Vlčkov, Czech Republic since July, 2010 has shown that the unique features of this new *Lonicera* plant are stable and reproduced true to type in successive generations of asexual reproduction.

SUMMARY OF THE INVENTION

Plants of the new *Lonicera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dolce Vita'. These characteristics in combination distinguish 'Dolce Vita' as a new and distinct *Lonicera* plant:

1. Upright and outwardly spreading plant habit.
2. Vigorous growth habit and rapid growth rate.
3. Early and freely fruiting habit.
4. Large flavorful dark blue-colored fruits.
5. Good garden performance.

Plants of the new *Lonicera* can be compared to plants of the female parent selection. In side-by-side comparisons, plants of the new *Lonicera* differ primarily from plants of the female parent selection in the following characteristics:

1. Plants of the new *Lonicera* are larger and more vigorous than plants of the female parent selection.
2. Plants of the new *Lonicera* have larger leaves than plants of the female parent selection.
3. Plants of the new *Lonicera* produce more fruits than plants of the female parent selection.
4. Fruits of plants of the new *Lonicera* are larger, more flavorful and more persistent than fruits of plants of the female parent selection.

Plants of the new *Lonicera* can be compared to plants of the male parent selection. In side-by-side comparisons, plants of the new *Lonicera* differ primarily from plants of the male parent selection in the following characteristics:

1. Plants of the new *Lonicera* produce more fruits than plants of the male parent selection.
2. Fruits of plants of the new *Lonicera* are more flavorful and more persistent than fruits of plants of the male parent selection.

Plants of the new *Lonicera* can be compared to plants of *Lonicera caerulea* 'Amur', not patented. In side-by-side comparisons plants of the new *Lonicera* differed primarily from plants of 'Amur' in the following characteristics:

1. Plants of the new *Lonicera* were larger than plants of 'Amur'.
2. Fruits of plants of the new *Lonicera* were larger, more flavorful and more persistent than fruits of plants of 'Amur'.

Plants of the new *Lonicera* can be compared to plants of *Lonicera caerulea* 'Altaj', not patented. In side-by-side comparisons plants of the new *Lonicera* differed primarily from plants of 'Altaj' in the following characteristics:

1. Plants of the new *Lonicera* were larger than plants of 'Altaj'.
2. Plants of the new *Lonicera* fruited later than plants of 'Altaj'.
3. Fruits of plants of the new *Lonicera* were larger, more flavorful and more persistent than fruits of plants of 'Amur'.

BRIEF DESCRIPTION OF THE PHOTOGRAPHS

The accompanying colored photographs illustrate the overall appearance of the new *Lonicera* plant showing the colors as true as it is reasonably possible to obtain in colored reproductions of this type. Colors in the photographs may differ slightly from the color values cited in the detailed botanical description which accurately describe the colors of the new *Lonicera* plant.

The photograph on the first sheet is a side perspective view of typical plants of 'Dolce Vita' grown in an outdoor nursery.

The photograph on the second sheet is a close-up view of a typical flowers of 'Dolce Vita'.

The photograph on the third sheet is a close-up view of typical fruits of 'Dolce Vita'.

DETAILED BOTANICAL DESCRIPTION

The aforementioned photographs and following observations, measurements and values describe plants grown in three-gallon containers and ground beds during the spring in a polyethylene-covered greenhouse in Grand Haven, Mich. and under cultural practices typical of commercial *Lonicera* production. During the production of the plants, day temperatures ranged from 20° C. to 32° C. and night temperatures ranged from 12° C. to 20° C. Plants were one year old when the photographs and the description were taken. In the description, color references are made to The Royal Horticultural Society Colour Chart, 2007 Edition, except where general terms of ordinary dictionary significance are used.

Botanical classification: *Lonicera caerulea* var. *Kamtschatica* 'Dolce Vita'.

Parentage:

*Female, or seed, parent*.—Unnamed seedling selection of *Lonicera caerulea* var. *Kamtschatica*, not patented.

*Male, or pollen, parent*.—Unnamed seedling selection of *Lonicera caerulea* var. *Kamtschatica*, not patented.

Propagation:

*Type*.—By softwood cuttings.

*Time to initiate roots, summer*.—About ten days at temperatures about 26° C.

*Time to produce a rooted young plant, summer*.—About five weeks at temperatures about 26° C.

*Root description*.—Fine; light brown in color.

*Rooting habit*.—Freely branching; dense.

Plant description:

*Plant form and growth habit*.—Perennial deciduous shrub; upright and outwardly spreading plant habit; broad inverted triangle; vigorous growth habit and rapid growth rate.

*Branching habit*.—Moderately freely branching habit; about 24 lateral branches develop per plant; pinching enhances lateral branch development.

*Plant height*.—About 36 cm to 50 cm.

*Plant diameter* (*area of spread*).—About 60 cm.

Lateral branch description:

*Length*.—About 28 cm to 52 cm.

*Diameter*.—About 2.5 mm to 4 mm.

*Internode length*.—About 2 cm to 5 cm.

*Strength*.—Strong, sturdy.

*Aspect*.—Erect to about 45° from vertical.

*Texture, developing*.—Smooth, glabrous.

*Texture, developed*.—Pubescent.

*Color, developing, upper surface*.—Close to 173A.

*Color, developing, lower surface*.—Close to 145B.

*Color, fully developed, upper and lower surfaces*.—Close to 164A.

Leaf description:

*Arrangement*.—Opposite, simple.

*Length*.—About 4 cm to 5 cm.

*Width*.—About 1.5 cm.

*Shape*.—Lanceolate to elliptic.

*Apex*.—Acute.

*Base*.—Acute to oblique.

*Margin*.—Entire; slightly ciliate.

*Texture, upper and lower surfaces*.—Pubescent, slightly rough.

*Venation pattern*.—Pinnate.

*Color*.—Developing leaves, upper surface: Close to 146A. Developing leaves, lower surface: Close to 146B. Fully expanded leaves, upper and lower surfaces: Close to 147B; venation, close to 146C.

*Petioles*.—Length: About 1 mm to 2 mm. Diameter: About 0.5 mm to 1 mm. Texture, upper and lower surfaces: Smooth, glabrous. Color, upper and lower surfaces: Close to 146B.

Flower description:

*Flower appearance and arrangement*.—Narrowly campanulate flowers arranged in axillary pairs; freely flowering habit with about 45 flowers developing per lateral branch; flowers drooping.

*Fragrance*.—None detected.

*Natural flowering season*.—Plants flower continuously during the early spring in Michigan; flowers not persistent.

*Flower diameter*.—About 7 mm.

*Flower length*.—About 1.2 cm.

*Flower buds*.—Length: About 1 cm. Diameter: About 2 mm to 3 mm. Shape: Club-shaped. Color: Close to 145A.

*Petals*.—Quantity and arrangement: Five fused with apices free. Length: About 4 mm. Width: About 3 mm. Shape: Narrowly lanceolate. Apex: Slightly obtuse. Margin: Entire. Texture, upper and lower surfaces: Smooth, glabrous; slightly ruffled. Color: When opening, upper and lower surfaces: Close to 150D. Fully opened, upper and lower surfaces: Close to 150D.

*Sepals*.—Quantity and arrangement: Five in a single whorl. Length: About 3 mm. Width: About 1 mm. Shape: Lanceolate. Apex: Broadly acute. Margin: Entire. Texture, upper and lower surfaces: Smooth, glabrous. Color, upper and lower surfaces: Close to 146A.

*Peduncles*.—Length: About 3 mm. Diameter: About 0.5 mm. Strength: Strong. Texture: Smooth, glabrous. Color: Close to 146B.

*Reproductive organs*.—Stamens: Quantity per flower: Five. Anther length: About 2 mm. Anther shape: Lanceolate. Anther color: Close to 11A. Pollen amount: Moderate. Pollen color: Close to 11A. Pistils: Quantity per flower: One. Pistil length: About 1.5 cm.

Stigma shape: Round. Stigma color: Close to 150B. Style length: About 1.5 cm. Style color: Close to 4D.

*Fruits*.—Length: About 2.4 cm. Diameter: About 1 cm. Shape: Oblong. Texture: Smooth, glabrous; glaucous. Color: Close to 103A to 103D. Flavor: Sweet, blueberry-like.

Garden performance: Plants of the new *Lonicera* have been observed to have good garden performance and to tolerate rain, wind and to tolerate temperatures ranging from −32° C. to 40° C.

Pathogen & pest resistance: Plants of the new *Lonicera* have not been shown to be resistant to pathogens and pests common to *Lonicera* plants.

It is claimed:

1. A new and distinct *Lonicera* plant named 'Dolce Vita' as illustrated and described.

* * * * *

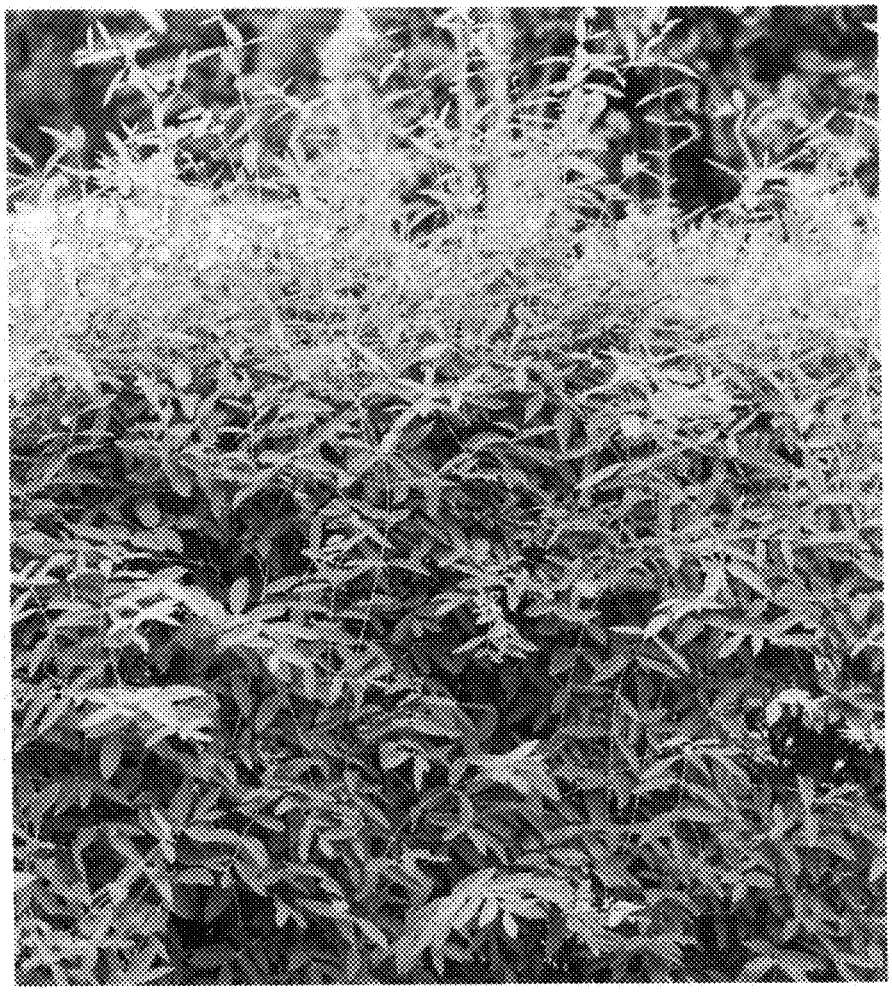

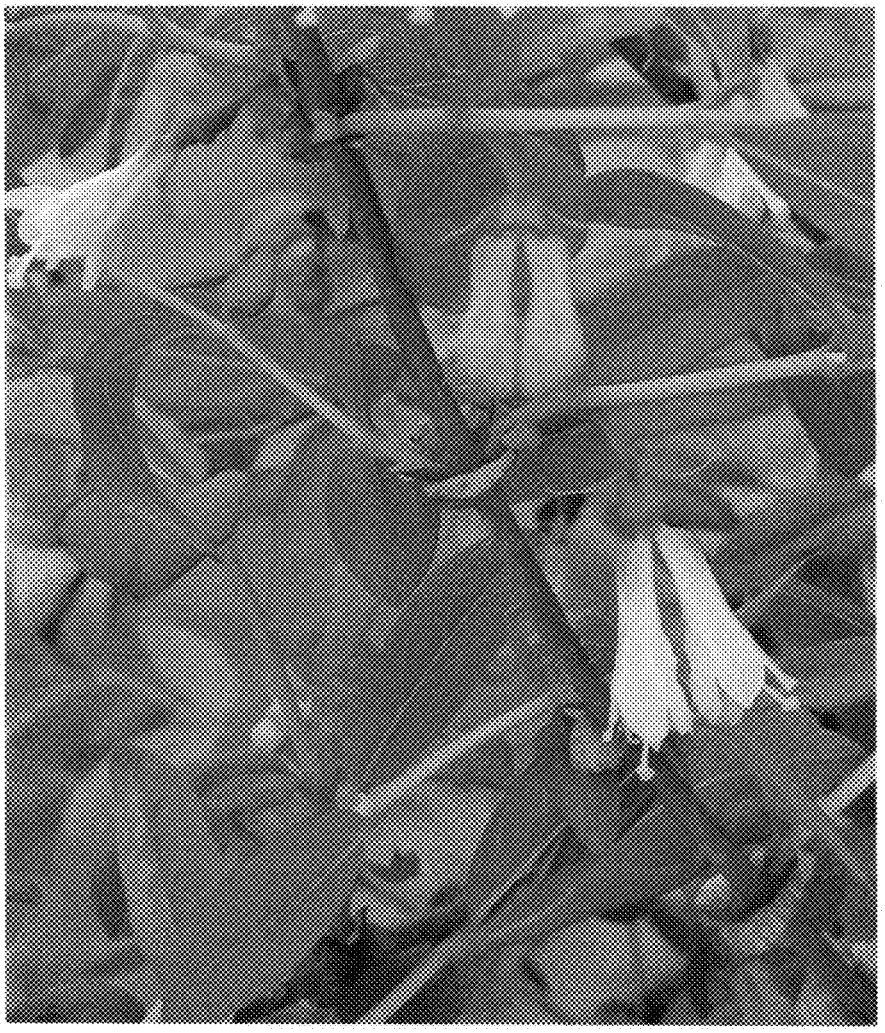

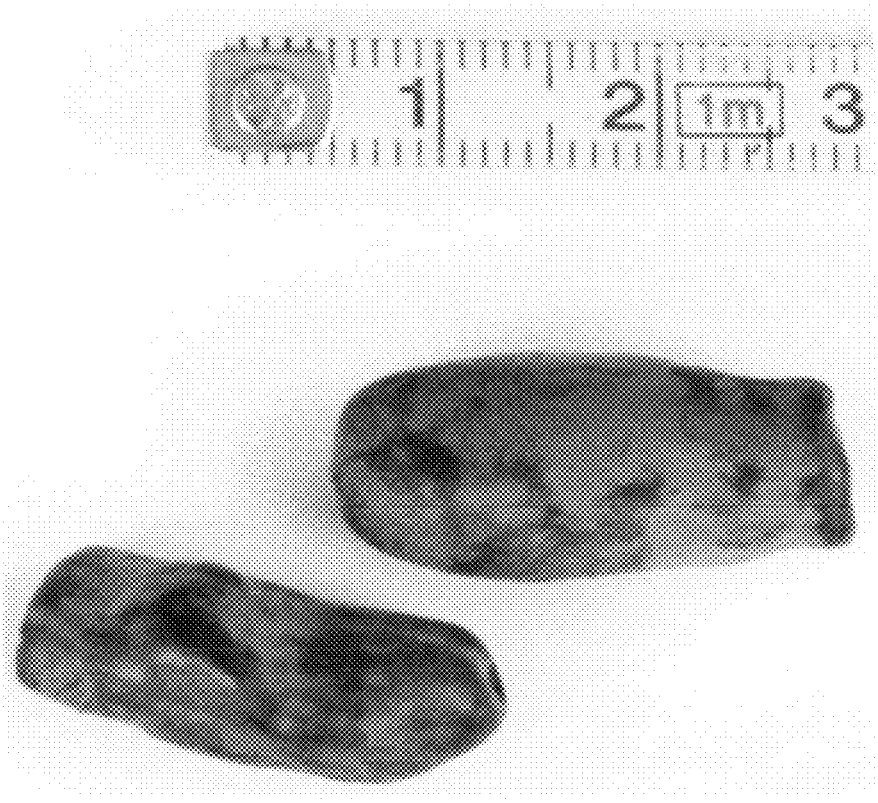
1
2
1m
3